(12) United States Patent
Li et al.

(10) Patent No.: US 9,428,496 B2
(45) Date of Patent: Aug. 30, 2016

(54) THIAZOLAMINE DERIVATIVE AND USE THEREOF AS ANTI-PICORNAVIRAL INFECTION MEDICAMENT

(75) Inventors: Song Li, Beijing (CN); Hongliang Wang, Beijing (CN); Junhai Xiao, Beijing (CN); Xian Zhang, Beijing (CN); Lili Wang, Beijing (CN); Zhibing Zheng, Beijing (CN); Wu Zhong, Beijing (CN); Yunde Xie, Beijing (CN); Xingzhou Li, Beijing (CN); Xinbo Zhou, Beijing (CN); Guoming Zhao, Beijing (CN); Xiaokui Wang, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 310 days.

(21) Appl. No.: 13/991,534

(22) PCT Filed: Dec. 6, 2011

(86) PCT No.: PCT/CN2011/083525
§ 371 (c)(1),
(2), (4) Date: Jul. 10, 2013

(87) PCT Pub. No.: WO2012/075927
PCT Pub. Date: Jun. 14, 2012

(65) Prior Publication Data
US 2014/0080840 A1      Mar. 20, 2014

(30) Foreign Application Priority Data
Dec. 6, 2010   (CN) .......................... 2010 1 0574544

(51) Int. Cl.
C07D 417/04   (2006.01)
A61K 31/496   (2006.01)
C07D 277/42   (2006.01)

(52) U.S. Cl.
CPC ............ *C07D 417/04* (2013.01); *A61K 31/496* (2013.01); *C07D 277/42* (2013.01)

(58) Field of Classification Search
None
See application file for complete search history.

(56) References Cited

FOREIGN PATENT DOCUMENTS

| EP | 0 398 425 A1 | 11/1990 |
| WO | WO 00/06558 A1 | 2/2000 |

OTHER PUBLICATIONS

Stefanachi, A et al., "1-, 3- and 8-substituted-9-deazaxanthines as potent and selective antagonists at the human $A_{2B}$ adenosine receptor," Bioorg Med Chem, Mar. 2008; 16(6): 2852-2869, Elsevier Science, Oxford, England.

Notification of the First Office Action, for Chinese Patent Appl. No. 201010574544.0, dated Mar. 7, 2014, State Intellectual Property Office of the People's Republic of China, Beijing, China.

Extended European search report including the supplementary European search report and the European search opinion, for EP patent application No. 11847007.9, dated Apr. 4, 2014.

International Search Report (ISR) for PCT/CN2011/083525; I.A. fd: Dec. 6, 2011, mailed Mar. 15, 2012 form the State Intellectual Property Office of the P.R. China, Beijing, China.

International Preliminary Report on Patentability (IPRP), Chapter I of the Patent Cooperation Treaty, including the Written Opinion for PCT/CN2011/083525; I.A. fd: Dec. 6, 2011, issued Jun. 12, 2013, from the International Bureau of WIPO, Geneva, Switzerland.

*Primary Examiner* — Savitha Rao
*Assistant Examiner* — Gregg Polansky
(74) *Attorney, Agent, or Firm* — Sterne, Kessler, Goldstein & Fox P.L.L.C.

(57) ABSTRACT

Disclosed is as a substituted thiazolamine derivative represented by Formula I or a pharmaceutically acceptable salt thereof or a hydrate thereof (the definitions of each group in the formula are as presented in the description), and the application thereof in the prevention and/or treatment of viral diseases induced by picornavirus. Also disclosed is a pharmaceutical composition containing the compound.

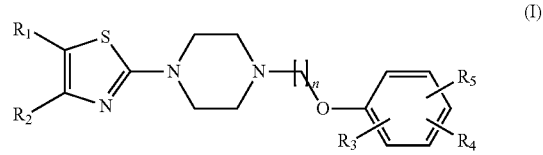

(I)

3 Claims, No Drawings

THIAZOLAMINE DERIVATIVE AND USE THEREOF AS ANTI-PICORNAVIRAL INFECTION MEDICAMENT

TECHNICAL FIELD

The present invention relates to substituted a thiazolamine derivative or a pharmaceutically acceptable salt or hydrate thereof, pharmaceutical composition containing the same, and use thereof as anti-picornaviral infection medicament in the prevention and/or treatment of viral diseases induced by picornavirus.

BACKGROUND ART

Picornavirus family is the smallest known animal RNA viruses. It consists of seven genera, i.e., the rhinovirus genus, enterovirus genus, aphthovirus genus, cardiovirus genus, hepatovirus genus, and double echovirus genus, in addition to some unsorted picornaviruses. The picornaviruses can induce diseases in multiple systems, for example, respiratory diseases, hand, foot and mouth disease, meningitis/encephalitis, acute poliomyelitis, cardiovascular diseases, hemorrhagic conjunctivitis, and hepatitis, etc.

In the late 1980's, there was a great progress in virology. Several important events in the viral life cycle have been commendably depicted. Many molecular targets have also been validated. Along with the occurrence of many new antiviral drugs, the development of virology also reaches the climax in recent years. Picornavirus inhibitors are being subjected to the study of activity. These inhibitors are targeting to the adsorption/uncoating process of viral protein 1 (VP1), a relatively conservative capsid structure mediated virus. The VP1 of viruses of different serotypes is of highly conservative structure, but it is necessary for viral replication. The inhibitor that acts on this target may become anti-picornaviral medicament.

CONTENTS OF THE INVENTION

The object of the present invention is to find a new type of small molecule compound acting on VP1, which can prevent the adhesion and uncoating of virus, so as to achieve the purpose of preventing and/or treating of diseases induced by picornaviruses.

After study, the present inventor has found that the compound having the following general formula I can act on VP1 of picornavirus to prevent the adhesion and uncoating of virus, and therefore is useful for the prevention and/or treatment of diseases induced by picornaviruses.

The first aspect of the present invention relates to a compound of formula I or a pharmaceutically acceptable salt or hydrate thereof:

I 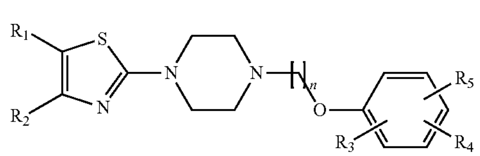 wherein:

$R_1$ and $R_2$ are each independently hydrogen, halogen, $C_1$-$C_8$ straight or branched chain alkyl;

n is 2, 3, 4, 5 or 6;

$R_3$, $R_4$ and $R_5$ are each independently hydrogen, halogen, $C_1$-$C_8$ straight or branched chain alkyl, —$COOR_7$ or —$OR_8$; and $R_7$ and $R_8$ are each independently hydrogen, or $C_1$-$C_6$ straight or branched chain alkyl.

According to the present invention, the compound of formula I or the pharmaceutically acceptable salt or hydrate thereof is preferably selected from the following compounds:

2-{4-[5-(4-methoxyphenoxy)pentyl]-piperazin-1-yl}thiazole,
2-{4-[5-(4-ethoxyphenoxy)pentyl]piperazin-1-yl}thiazole,
2-{4-[5-(4-fluorophenoxy)pentyl]-piperazin-1-yl}thiazole,
2-{4-[5-(4-ethylphenoxy)pentyl]piperazin-1-yl}thiazole,
2-{4-[5-(4-isopropylphenoxy)pentyl]piperazin-1-yl}thiazole,
2-{4-[5-(4-tert-butylphenoxy)pentyl]piperazin-1-yl}thiazole,
2-{4-[5-(4-methylphenoxy)pentyl]piperazin-1-yl}thiazole,
2-{4-[6-(4-methylphenoxy)hexyl]piperazin-1-yl}thiazole,
2-{4-[6-(4-ethylphenoxy)hexyl]piperazin-1-yl}thiazole,
2-[4-(6-phenoxyhexyl)piperazin-1-yl]thiazole,
2-{4-[6-(4-tert-butylphenoxy)hexyl]piperazin-1-yl}thiazole,
2-{4-[6-(4-fluorophenoxy)hexyl]piperazin-1-yl}thiazole,
2-{4-[6-(4-chlorophenoxy)hexyl]piperazin-1-yl}thiazole,
2-{4-[6-(4-bromophenoxy)hexyl]piperazin-1-yl}thiazole,
5-{4-[3-(4'-ethoxybiphenyl-4-oxy)pentyl]piperazin-1-yl}thiazole,
2-{4-[5-(4-chlorophenoxy)pentyl]piperazin-1-yl}thiazole,
2-{4-[5-(4-bromophenoxy)pentyl]piperazin-1-yl}thiazole,
2-{4-[5-(4-bromophenoxy)pentyl]piperazin-1-yl}thiazole hydrochloride,
2-[4-(5-phenoxypentyl)piperazin-1-yl]thiazole hydrochloride,
2-{4-[6-(4-methoxyphenoxy)hexyl]piperazin-1-yl}thiazole hydrochloride,
2-{4-[6-(4-ethoxyphenoxy)hexyl]piperazin-1-yl}thiazole hydrochloride,
2-{4-[6-(4-ethylphenoxy)hexyl]piperazin-1-yl}thiazole hydrochloride, and
2-{4-[6-(4-isopropylphenoxy)hexyl]piperazin-1-yl}thiazole hydrochloride.

The second aspect of the present invention relates to a pharmaceutical composition comprising at least one compound of formula I or a pharmaceutically acceptable salt or hydrate thereof and one or more pharmaceutically acceptable carriers or excipients.

The third aspect of the present invention relates to use of a compound of formula I or a pharmaceutically acceptable salt or hydrate thereof in the preparation of a medicament for the prevention and/or treatment of diseases associated with picornaviral infection.

The fourth aspect of the present invention relates to a method for the prevention and/or treatment of diseases associated with picornaviral infection, which comprises administering a prophylactically and/or therapeutically effective amount of at least one compound of formula I or a pharmaceutically acceptable salt or hydrate thereof to a patient in need of the prevention and/or treatment of diseases associated with picornaviral infection.

The fifth aspect of the present invention relates to a compound of formula I or a pharmaceutically acceptable salt or hydrate thereof useful for the prevention and/or treatment of diseases associated with picornaviral infection.

According to the present invention, the compound of formula I or a pharmaceutically acceptable salt or hydrate thereof is preferably selected from the following compounds:

2-{4-[5-(4-methoxyphenoxy)pentyl]-piperazin-1-yl}thiazole,
2-{4-[5-(4-ethoxyphenoxy)pentyl]piperazin-1-yl}thiazole,
2-{4-[5-(4-fluorophenoxy)pentyl]-piperazin-1-yl}thiazole,
2-{4-[5-(4-ethylphenoxy)pentyl]piperazin-1-yl}thiazole,
2-{4-[5-(4-isopropylphenoxy)pentyl]piperazin-1-yl}thiazole,
2-{4-[5-(4-tert-butylphenoxy)pentyl]piperazin-1-yl}thiazole,
2-{4-[5-(4-methylphenoxy)pentyl]piperazin-1-yl}thiazole,
2-{4-[6-(4-methylphenoxy)hexyl]piperazin-1-yl}thiazole,
2-{4-[6-(4-ethylphenoxy)hexyl]piperazin-1-yl}thiazole,
2-[4-(6-phenoxyhexyl)piperazin-1-yl]thiazole, 2-{4-[6-(4-tert-butylphenoxy)hexyl]piperazin-1-yl}thiazole,
2-{4-[6-(4-fluorophenoxy)hexyl]piperazin-1-yl}thiazole,
2-{4-[6-(4-chlorophenoxy)hexyl]piperazin-1-yl}thiazole,
2-{4-[6-(4-bromophenoxy)hexyl]piperazin-1-yl}thiazole,
5-{4-[3-(4'-ethoxybiphenyl-4-oxy)pentyl]piperazin-1-yl}thiazole,
2-{4-[5-(4-chlorophenoxy)pentyl]piperazin-1-yl}thiazole,
2-{4-[5-(4-bromophenoxy)pentyl]piperazin-1-yl}thiazole,
2-{4-[5-(4-bromophenoxy)pentyl]piperazin-1-yl}thiazole hydrochloride,
2-[4-(5-phenoxypentyl)piperazin-1-yl]thiazole hydrochloride,
2-{4-[6-(4-methoxyphenoxy)hexyl]piperazin-1-yl}thiazole hydrochloride,
2-{4-[6-(4-ethoxyphenoxy)hexyl]piperazin-1-yl}thiazole hydrochloride,
2-{4-[6-(4-ethylphenoxy)hexyl]piperazin-1-yl}thiazole hydrochloride, and
2-{4-[6-(4-isopropylphenoxy)hexyl]piperazin-1-yl}thiazole hydrochloride.

According to the present invention, the compound of formula I can be prepared by the following reaction scheme:

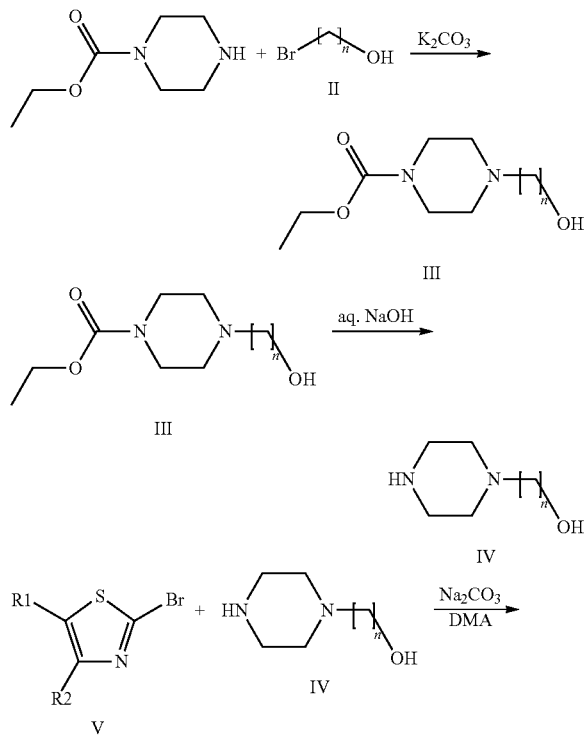

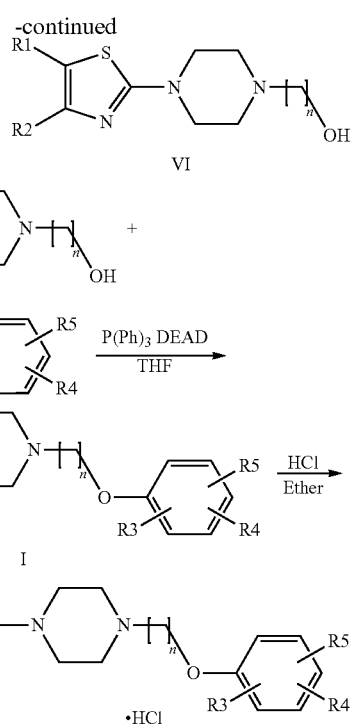

Ethyl N-piperazinecarboxylate and a compound of formula II are reacted at room temperature in the presence of potassium carbonate using acetonitrile as solvent, to obtain a compound of formula III; the compound of formula III is heated under reflux in the presence of a 10% aqueous solution of sodium hydroxide using ethanol as solvent, to obtain a compound of formula IV; a compound of formula V and the compound of formula IV are reacted at room temperature in the presence of sodium carbonate using chloroform, acetone, dichloromethane, N,N-dimethylformamide, N,N-dimethylacetamide (preferably N,N-dimethylacetamide) as solvent, to obtain a compound of general formula VI; the compound of general formula VI and a compound of general formula VII are reacted at room temperature in the presence of triphenylphosphine and diethyl azodicarboxylate using tetrahydrofuran as solvent, to obtain a compound of formula I; the compound of formula I is reacted at room temperature in the presence of a saturated solution of hydrogen chloride-diethyl ether using acetone as solvent, to obtain the corresponding hydrochloride salt of the compound of formula I.

According to the present invention, the term "pharmaceutically acceptable salt" of the compound of the present invention includes acid salts formed by the compound of the present invention with pharmaceutically acceptable inorganic or organic acids or base salts formed by pharmaceutically acceptable bases therewith. Wherein, the acid salts include, but are not limited to: hydrochloride, hydrobromide, hydroiodide, nitrate, sulfate, bisulfate, phosphate, biphosphate, acetate, propionate, butyrate, oxalate, 3-methylacetate, adipate, alginate, lactate, citrate, tartrate, succinate, maleate, fumarate, picrate, aspartate, gluconate, benzoate, methanesulfonate, ethanesulfonate, benzenesulfonate, p-toluenesulfonate and pamoate; base salts include, but are not limited to: ammonium salts, alkali metal salts such as sodium and potassium salts, alkaline earth metal salts such as calcium and magnesium salts, organic base salts such as dicyclohexylamine and N-methyl-D-glucamine salts, and amino acid salts such as arginine and lysine salts.

According to the present invention, the pharmaceutical composition comprises an effective amount of a compound of formula I or a pharmaceutically acceptable salt or hydrate thereof and one or more suitable pharmaceutically acceptable carrier. The pharmaceutically acceptable carrier herein includes, but not limited to: ion exchangers, alumina, aluminum stearate, lecithin, serum proteins such as human serum albumin, buffer agents such as phosphates, glycerine, sorbic acid, potassium sorbate, partial glyceride mixture of saturated vegetable fatty acids, water, salts or electrolytes, such as protamine sulfate, disodium hydrogen phosphate, potassium biphosphate, sodium chloride, zinc salts, colloidal silica, magnesium trisilicate, polyvinylpyrrolidone, cellulose substances, polyethylene glycol, sodium carboxymethylcellulose, polyacrylates, beeswax, polyethylene-polyoxypropylene block polymer, and lanolin.

The compounds of the present invention are a type of potent inhibitors of picornaviruses. The outstanding characteristic of this type of compounds resides in that they can not only prevent but also treat diseases induced by picornaviruses. The diseases induced by picornaviruses include, but are not limited to: respiratory diseases, hand, foot and mouth disease, meningitis/encephalitis, acute poliomyelitis, cardiovascular diseases, hemorrhagic conjunctivitis, hepatitis and so on.

The diseases induced by enteroviruses comprise, but are not limited to: hand, foot and mouth disease, myocarditis, respiratory infection, pulmonary edema, aseptic meningitis, brainstem encephalitis and poliomyelitis-like paralysis and the like. Such lesions are generally induced by enterovirus EV71 and Coxsackie virus A16 belonging to the family of picornavirus.

According to the present invention, the pharmaceutical composition comprising the compound of the present invention can be administered according to any of the following routes: oral, spray inhalation, rectal, nasal, buccal, vaginal, topical, parenteral such as subcutaneous, intravenous, intramuscular, intraperitoneal, intrathecal, intraventricular, intrasternal or intracranial injection or infusion, or by means of an explanted reservoir, wherein oral, intraperitoneal or intravenous administration route is preferred. Further, in order to make the compound of the present invention be effective for the treatment of central nervous system disorders, intraventricular administration route is preferred so as to avoid the possible low blood brain barrier permeability of the compound.

For oral administration, the compound of the present invention can be made into any orally acceptable preparation form, including, but not limited to, tablets, capsules, aqueous solution or aqueous suspension. Wherein, the carriers as generally used for tablets include lactose and corn starch, and additionally a lubricant such as magnesium stearate may also be added. The diluents as generally used for capsule preparations include lactose and dried corn starch. Aqueous suspension preparations are usually used by mixing active ingredient with a suitable emulsifying agent and suspending agent. If required, some sweeteners, flavoring agents or coloring agents may also be added in the above oral preparation forms.

For rectal administration, the compound of the present invention is generally made into the form of suppository, which is prepared by mixing the drug with a suitable non-irritating excipient. The excipient is in a solid state at room temperature, but melts at rectal temperature and releases drug. Such excipient includes cacao butter, beeswax and polyethylene glycol.

For topical administration, in particular for the treatment of affected surfaces or organs that are easy to reach by local application, for example, eyes, skin or lower intestinal neurological diseases, the compound of the present invention can be made into different topical preparation forms according to different affected surfaces or organs. It is specifically described as follows:

For ocular topical application, the compound of the present invention can be formulated into the preparation form of a micronised suspension or solution. The carrier used is an isotonic sterile saline of a certain pH, in which a preservative such as benzyl chloride alkoxide can be added or not. In addition, for the application to eyes, the compound can also be made into the form of ointments, such as vaseline ointment.

For topical administration on skin, the compound of the present invention can be made into an appropriate form of ointments, lotions, or creams, wherein the active ingredient is suspended or dissolved in one or more carriers. The carrier that can be used in ointments includes, but not limited to, mineral oil, liquid petrolatum, white petrolatum, propylene glycol, polyoxyethylene, polyoxypropylene, emulsifying wax and water; the carrier that can be used in lotions and creams includes, but not limited to, mineral oil, sorbitan monostearate, Tween 60, cetyl ester wax, hexadecene aryl alcohol, 2-octyldodecanol, benzyl alcohol and water.

For lower intestinal topical application, the compound of the present invention can be made into a rectal suppository preparation form as described above or a suitable enema preparation form. In addition, a local transdermal patch can also be used.

The compound of the present invention can also be administered in the form of sterile injectable preparations, including sterile injectable aqueous or oily suspensions, or sterile injectable solutions. Wherein, carriers and solvents that can be used include water, Ringer's solution and isotonic sodium chloride solution. In addition, sterilized non-volatile oil, such as monoglycerides or diglycerides, can also be used as a solvent or suspending medium.

Also to be noted, the specific dosages and use methods of the compound of the present invention directed to different patients depend on many factors, including the patient's age, weight, gender, natural health status, nutritional status, activity level of the compound, use time, metabolic rate, severity of disease and subjective judgment of physician. It is preferred that the dosage is between 0.01 and 100 mg/kg body weight/day.

MODE OF CARRYING OUT THE INVENTION

The following examples are preferred embodiments used to illustrate the present invention, but do not restrict the present invention in any manner.

Melting point of the compound is determined by RY-1 type melting point apparatus, wherein thermometer is not corrected. $^1$H NMR is determined by Japan Electronics JNM-ECA-400 type NMR spectrometer. Mass spectrum is determined by Agilent 5875 (EI) and API3000 (ESI) type mass spectrometers. If not indicated, the solvents used in all reactions have been subjected to standard pretreatment.

Example 1

2-{4-[5-(4-methoxyphenoxy)pentyl]piperazin-1-yl}thiazole

1.1 Synthesis of ethyl 4-(5-hydroxypentyl)piperazinecarboxylate

Ethyl N-piperazinecarboxylate (25.50 g, 161.39 mmol), 5-bromo-1-pentanol (26.96 g, 161.39 mmol), potassium carbonate (55.68 g, 403.48 mmol) and anhydrous acetonitrile (200 mL) were placed in a 500 mL round-bottomed flask and heated under reflux with stirring overnight; the reaction system was cooled down to room temperature, filtered, concentrated and separated by column chromatography (eluent: dichloromethane/methanol/triethylamine system, v/v/v 100:1:0.5), to obtain a pale yellow oil 20.48 g, yield 52.0% (which was directly used in the next step reaction).

1.2 Synthesis of 1-(5-hydroxypentyl)piperazine

Ethyl 4-(5-hydroxypentyl)piperazinecarboxylate (10.87 g, 65.09 mmol), 10% aqueous sodium hydroxide solution (150 mL) and ethanol (150 mL) were placed in a 500 mL round-bottomed flask, and heated under reflux with stirring overnight; the reaction system was cooled down to room temperature, and the solvent was distilled off under reduced pressure, to obtain a pale yellow oil; to the oil, 200 ml of saturated brine was added, followed by extraction with dichloromethane (5×200 mL); the resulting extract was dried with $Na_2SO_4$, filtered, and concentrated to obtain a pale yellow oil 9.69 g, yield 86.5% (which was directly used in the next step reaction).

1.3 Synthesis of 5-[4-(thiazol-2-yl)piperazin-1-yl]-pentyl-1-ol

2-Bromothiazole (12.30 g, 75 mmol), sodium carbonate (5.30 g, 50 mmol) and DMF (40 mL) were placed in a 150 mL three-necked flask, to which a solution of 1-(5-hydroxypentyl)piperazine (8.60 g, 50 mmol) in DMF (10 mL) was slowly added dropwise under ice-bath conditions within 30 min, followed by reacting at 80° C. with stirring overnight; thereafter, the solvent was distilled off under reduced pressure, to obtain a yellow solid, which was washed with diethyl ether (3×50 mL) and recrystallized (petroleum ether), to obtain a white solid 5.95 g, yield 46.5%.

1.4 Synthesis of 2-{4-[5-(4-methoxyphenoxy)pentyl]piperazin-1-yl}thioazole

5-[4-(thiazol-2-yl)piperazin-1-yl]-pentyl-1-ol (0.51 g, 2 mmol), p-methoxyphenol (0.22 g, 2 mmol), triphenylphosphine (0.52 g, 2 mmol) and anhydrous THF (10 mL) were placed in a 50 mL three-necked flask, to which DEAD (0.35 g, 2 mmol) was slowly added dropwise under ice-bath conditions within 10 min, followed by reacting at room temperature with stirring overnight; thereafter, the reaction mixture was separated by column chromatography (eluent: petroleum ether/acetone system, v/v 15:1), to obtain a white solid 0.15 g, yield 20.7%.

mp: 83-85° C.; $^1$H-NMR (400 MHz, $CDCl_3$, δ ppm) δ 1.50-1.60 (m, 4H), 1.80 (m, 2H), 2.42 (br, 1H), 2.57 (br, 3H), 3.52 (br, 3H), 3.77 (s, 3H), 3.92 (t, 2H, J=6.4 Hz), 6.58 (d, 1H, J=3.2 Hz), 6.83 (s, 4H), 7.20 (d, 1H, J=3.6 Hz); EI-MS (m/z): 361.2 $[M-H]^+$.

The following compounds can be prepared according to the same method as described in step 1.4 of Example 1, by using different reactants (various substituted phenols) in place of p-methoxyphenol used in step 1.4 of Example 1.

Example 2

2-{4-[5-(4-ethoxyphenoxy)pentyl]piperazin-1-yl}thiazole

According to the same method as described in step 1.4 of Example 1, the titled compound was obtained, which was a white solid, yield 33.3%. mp: 79-81° C.; $^1$H-NMR (400 MHz, $CDCl_3$, δ ppm) δ1.39 (t, 3H), 1.49-1.60 (m, 4H), 1.49-1.60 (m, 4H), 1.79 (m, 2H), 2.43 (br, 2H), 2.57 (br, 4H), 3.52 (br, 4H), 3.90-4.00 (m, 4H), 6.57 (d, 1H, J=3.2 Hz), 6.82 (s, 4H), 7.20 (d, 1H, J=3.6 Hz); EI-MS (m/z): 375.2 $[M-H]^+$.

Example 3

2-{4-[5-(4-fluorophenoxy)pentyl]piperazin-1-yl}thiazole

According to the same method as described in step 1.4 of Example 1, the titled compound was obtained, which was a white solid, yield 20.8%. mp: 42-44° C.; $^1$H-NMR (400 MHz, $CDCl_3$, δ ppm) δ1.50-1.61 (m, 4H), 1.81 (m, 2H), 2.43 (m, 2H), 2.58 (br, 4H), 3.52 (br, 4H), 3.92 (t, 2H, J=6.8 Hz), 6.58 (d, 1H, J=3.6 Hz), 6.80-6.84 (m, 2H), 6.94-6.99 (m, 2H), 7.20 (d, 1H, J=3.6 Hz); EI-MS (m/z): 349.2 $[M-H]^+$.

Example 4

2-{4-[5-(4-ethylphenoxy)pentyl]piperazin-1-yl}thiazole

According to the same method as described in step 1.4 of Example 1, the titled compound was obtained, which was a white solid, yield 22.3%. mp: 125-127° C.; $^1$H-NMR (400 MHz, $CDCl_3$, δ ppm) δ 1.21 (t, 3H), 1.50-1.60 (m, 4H), 1.81 (m, 2H), 2.42 (m, 2H), 2.58 (m, 6H), 3.52 (br, 4H), 3.94 (t, 2H), 6.57 (d, 1H, J=3.6 Hz), 6.78-6.83 (m, 2H), 7.10 (d, 2H, J=8.8 Hz), 7.20 (d, 1H, J=3.6 Hz); EI-MS (m/z): 359.2 $[M-H]^+$.

Example 5

2-{4-[5-(4-isopropylphenoxy)pentyl]piperazin-1-yl}thiazole

According to the same method as described in step 1.4 of Example 1, the titled compound was obtained, which was a white solid, yield 26.8%. mp: 128-130° C.; $^1$H-NMR (400 MHz, $CDCl_3$, δ ppm) δ 1.22 (d, 6H, J=7.2 Hz), 1.50-1.60 (m, 4H), 1.81 (m, 2H), 2.43 (m, 2H), 2.57 (m, 4H), 2.86 (m, 1H) 3.52 (br, 4H), 3.94 (t, 2H), 6.58 (d, 1H, J=3.2 Hz), 6.82 (d, 2H, J=8.4 Hz), 7.14 (d, 2H, 1=8.4 Hz), 7.20 (d, 1H, J=3.2 Hz); EI-MS (m/z): 373.3 $[M-H]^+$.

Example 6

2-{4-[5-(4-tert-butylphenoxy)pentyl]piperazin-1-yl}thiazole

According to the same method as described in step 1.4 of Example 1, the titled compound was obtained, which was a white solid, yield 28.5%. mp: 125-127° C.; $^1$H-NMR (400 MHz, CDCl$_3$, δ ppm) δ 1.30 (s, 9H), 1.49-1.61 (m, 4H), 1.81 (m, 2H), 2.44 (br, 2H), 2.58 (br, 4H), 3.53 (br, 4H), 3.95 (t, 2H, J=6.0 Hz), 6.58 (d, 1H, J=3.6 Hz), 6.83 (d, 2H, J=8.8 Hz), 7.20 (d, 1H, J=3.2 Hz), 7.30 (d, 2H, J=9.2 Hz); EI-MS (m/z): 387.3 [M–H]$^+$.

Example 7

2-{4-[5-(4-methylphenoxy)pentyl]piperazin-1-yl}thiazole

According to the same method as described in step 1.4 of Example 1, the titled compound was obtained, which was a white solid, yield 43.5%. mp: 125-127° C.; $^1$H-NMR (400 MHz, CDCl$_3$, δ ppm) δ 1.50-1.60 (m, 4H), 1.81 (m, 2H), 2.28 (s, 3H), 2.43 (br, 2H), 2.57 (br, 4H), 3.52 (br, 4H), 3.94 (t, 2H, J=6.4 Hz), 6.57 (d, 1H, J=3.6 Hz), 6.79 (d, 2H, J=11.6 Hz), 7.07 (d, 2H, J=8.0 Hz), 7.20 (d, 2H, J=3.6 Hz); EI-MS (m/z): 345.2 [M–H]$^+$.

Example 8

2-{4-[6-(4-methylphenoxy)hexyl]piperazin-1-yl}thiazole

According to the same method as described in step 1.4 of Example 1, the titled compound was obtained, which was a white solid, yield 40.4%. mp: 37-39° C.; $^1$H-NMR (400 MHz, CDCl$_3$, δ ppm) δ 1.39-1.51 (m, 6H), 1.78 (m, 2H), 2.28 (s, 3H), 2.42 (br, 1H), 2.58 (br, 4H), 3.53 (br, 4H), 3.94 (t, 2H, J=6.4 Hz), 6.58 (d, 1H, J=3.6 Hz), 6.79 (d, 2H, J=8.8 Hz), 7.07 (d, 2H, J=8.0 Hz), 7.20 (d, 1H, J=3.6 Hz); EI-MS (m/z): 359.3 [M–H]$^+$.

Example 9

2-{4-[6-(4-ethylphenoxy)hexyl]piperazin-1-yl}thiazole

According to the same method as described in step 1.4 of Example 1, the titled compound was obtained, which was a white solid, yield 40.2%. mp: 21-23° C.; $^1$H-NMR (400 MHz, CDCl$_3$, δ ppm) δ 1.21 (t, 3H), 1.39-1.57 (m, 6H), 1.78 (m, 2H), 2.41 (br, 2H), 2.59 (m, 6H), 3.53 (br, 4H), 3.93 (t, 2H, J=8.0 Hz), 6.57 (d, 1H, J=3.6 Hz), 6.82 (d, 2H, J=6.8 Hz), 7.10 (d, 2H, J=8.8 Hz), 7.20 (d, 1H, J=3.6 Hz); EI-MS (m/z): 373.3 [M–H]$^+$.

Example 10

2-[4-(6-phenoxyhexyl)piperazin-1-yl]thiazole

According to the same method as described in step 1.4 of Example 1, the titled compound was obtained, which was a white solid, yield 53.6%. mp: 37-39° C.; $^1$H-NMR (400 MHz, CDCl$_3$, δ ppm) δ 1.39-1.57 (m, 6H), 1.80 (m, 2H), 2.41 (t, 2H, J=7.2 Hz), 2.58 (br, 4H), 3.52 (br, 4H), 3.96 (t, 2H, J=6.4 Hz), 6.57 (d, 1H, J=3.6 Hz), 6.88-6.95 (m, 2H), 7.20-7.30 (m, 4H); EI-MS (m/z): 345.2 [M–H]$^+$.

Example 11

2-{4-[6-(4-tert-butylphenoxy)hexyl]piperazin-1-yl}thiazole

According to the same method as described in step 1.4 of Example 1, the titled compound was obtained, which was a white solid, yield 63.0%. mp: 30-32° C.; $^1$H-NMR (400 MHz, CDCl$_3$, δ ppm) δ 1.30 (s, 9H), 1.37-1.58 (m, 6H), 1.78 (m, 2H), 2.41 (br, 2H), 2.57 (br, 4H), 3.52 (br, 4H), 3.94 (t, 2H, J=6.4 Hz), 6.57 (d, 1H, J=3.6 Hz), 6.83 (d, 2H, J=8.8 Hz), 7.20 (d, 1H, J=3.6 Hz), 7.29 (t, 2H, J=2.0 Hz); EI-MS (m/z): 401.3 [M–H]$^+$.

Example 12

2-{4-[6-(4-fluorophenoxy)hexyl]piperazin-1-yl}thiazole

According to the same method as described in step 1.4 of Example 1, the titled compound was obtained, which was a white solid, yield 13.8%. mp: 58-60° C.; H-NMR (400 MHz, CDCl$_3$, δ ppm) δ 1.39-1.57 (m, 6H), 1.78 (m, 2H), 2.41 (br, 2H), 2.57 (br, 4H), 3.52 (br, 4H), 3.91 (t, 2H, J=6.4 Hz), 6.58 (d, 1H, J=3.6 Hz), 6.81-6.84 (m, 2H), 6.92 (m, 2H), 7.20 (d, 1H, J=3.6 Hz); EI-MS (m/z): 363.2 [M–H].

Example 13

2-{4-[5-(4-tert-butylphenoxy)pentyl]piperazin-1-yl}thiazole

According to the same method as described in step 1.4 of Example 1, the titled compound was obtained, which was a white solid, yield 39.6%. mp: 61-63° C.; $^1$H-NMR (400 MHz, CDCl$_3$, δ ppm) δ 1.39-1.56 (m, 6H), 1.79 (m, 2H), 2.40 (t, 2H, J=7.6 Hz), 2.57 (br, 4H), 3.52 (br, 4H), 3.92 (t, 2H, J=6.4 Hz), 6.57 (d, 1H, J=4.0 Hz), 6.82-6.80 (m, 2H), 7.20-7.23 (m, 3H); EI-MS (m/z): 379.2 [M–H]$^+$.

Example 14

2-{4-[6-(4-bromophenoxy)hexyl]piperazin-1-yl}thiazole

According to the same method as described in step 1.4 of Example 1, the titled compound was obtained, which was a white solid, yield 36.6%. mp: 66-68° C.; $^1$H-NMR (400 MHz, CDCl$_3$, δ ppm) δ 1.39-1.57 (m, 6H), 1.79 (m, 2H), 2.41 (br, 2H), 2.57 (br, 4H), 3.52 (br, 4H), 3.92 (t, 2H, J=6.4 Hz), 6.57 (d, 1H, J=3.6 Hz), 6.77 (d, 2H, J=8.8 Hz), 7.20 (d, 1H, J=3.6 Hz), 7.36 (d, 2H, J=8.4 Hz); EI-MS (m/z): 423.1 [M–H]$^+$.

Example 15

5-{4-[3-(4'-ethoxybiphenyl-4-oxy)pentyl]piperazin-1-yl}thiazole

According to the same method as described in step 1.4 of Example 1, the titled compound was obtained, which was a white solid, yield 14.9%. mp: 149-150° C.; $^1$H-NMR (400 MHz, CDCl$_3$, δ ppm) δ 1.53-1.62 (m, 4H), 1.84 (m, 2H), 2.45 (br, 2H), 2.58 (br, 4H), 3.53 (br, 4H), 3.85 (s, 3H), 4.00 (t, 2H, J=6.4 Hz), 6.58 (d, 1H, J=3.6 Hz), 6.95 (m, 4H), 7.20 (d, 1H, J=3.6 Hz), 7.47 (m, 4H); ESI-MS (m/z): 438.3 [M+H]$^+$.

Example 16

2-{4-[5-(4-tert-butylphenoxy)pentyl]piperazin-1-yl}thiazole

According to the same method as described in step 1.4 of Example 1, the titled compound was obtained, which was a white solid, yield 11.0%. mp: 71-73° C.; $^1$H-NMR (400 MHz, CDCl$_3$, δ ppm) δ 1.48-1.61 (m, 4H), 1.81 (m, 2H), 2.44 (br, 2H), 2.58 (br, 4H), 3.53 (br, 4H), 3.93 (t, 2H, J=6.4 Hz), 6.58 (d, 1H, J=3.6 Hz), 6.81 (d, 2H, J=6.4 Hz), 7.20-7.23 (m, 3H); EI-M S (m/z): 365.2 [M−H]$^+$.

Example 17

2-{4-[5-(4-bromophenoxy)pentyl]piperazin-1-yl}thiazole

According to the same method as described in step 1.4 of Example 1, the titled compound was obtained, which was a white solid, yield 9.8%. mp: 73-75° C.; $^1$H-NMR (400 MHz, CDCl$_3$, δ ppm) δ 1.47-1.61 (m, 4H), 1.81 (m, 2H), 2.43 (br, 2H), 2.58 (br, 4H), 3.53 (br, 4H), 3.93 (t, 2H, J=6.4 Hz), 6.58 (d, 1H, J=3.2 Hz), 6.77 (d, 2H, J=9.2 Hz), 7.20 (d, 1H, J=3.6 Hz), 7.36 (d, 2H, J=8.8 Hz); EI-MS (m/z): 409.1 [M−H]$^+$.

Example 18

2-{4-[5-(4-bromophenoxy)pentyl]piperazin-1-yl}thiazole hydrochloride

According to the same method as described in step 1.4 of Example 1, a white solid 0.08 g was obtained; the white solid was completely dissolved with acetone (10 mL), to which a saturated solution of HCl-diethyl ether was slowly added dropwise till pH=5, followed by filtering to obtain a white solid 0.08 g, yield 7.8%. mp: 221-223° C.; $^1$H-NMR (400 MHz, DMSO-d$_6$, δ ppm) δ 1.45 (m, 2H), 1.77 (m, 4H), 3.13 (m, 4H), 3.58 (t, 2H, J=10.4), 3.96-4.03 (m, 4H), 6.91 (d, 2H, J=9.2), 7.03 (d, 1H, J=3.6 Hz), 7.30 (d, 1H, J=−3.6 Hz), 7.44 (d, 2H, J=9.2 Hz), 11.27 (s, 1H); ESI-MS (m/z): 412.1 [M−2Cl]$^+$.

Example 19

2-[4-(5-phenoxypentyl)piperazin-1-yl]thiazole hydrochloride

According to the same method as described in step 1.4 of Example 1, a white solid 0.11 g was obtained; the white solid was completely dissolved with acetone (10 mL), to which a saturated solution of HCl-diethyl ether was slowly added dropwise till pH=5, followed by filtering to obtain a white solid 0.06 g, yield 7.42%. mp: 145-147° C.; $^1$H-NMR (400 MHz, DMSO-d$_6$, δ ppm) δ 1.46 (m, 2H), 1.78 (m, 4H), 3.15 (m, 4H), 3.56 (t, 4H, J=12.4), 3.96-4.02 (m, 4H), 6.92-6.94 (m, 3H), 7.03 (d, 1H, J=3.6 Hz), 7.28-7.30 (m, 3H), 11.20 (s, 1H); ESI-MS (m/z): 332.3 [M−2HCl]$^+$.

Example 20

2-{4-[6-(4-methoxyphenoxy)hexyl]piperazin-1-yl}thiazole hydrochloride

According to the same method as described in step 1.4 of Example 1, a white solid 0.30 g was obtained; the white solid was completely dissolved with acetone (10 mL), to which a saturated solution of HCl-diethyl ether was slowly added dropwise till pH=5, followed by filtering to obtain a white solid 0.31 g, yield 49.5%. mp: 221-223° C.; $^1$H-NMR (400 MHz, DMSO-d$_6$, δ ppm) δ 1.36-1.46 (m, 4H), 1.70-1.76 (m, 4H), 3.08-3.17 (m, 4H), 3.56-3.69 (m, 7H), 3.89 (t, 2H, J=6.4), 4.07 (d, 2H, J=13.6), 6.85 (s, 4H), 7.06 (d, 1H, J=4.0 Hz), 7.33 (d, 1H, J=4.0 Hz), 11.50 (s, 1H); ESI-MS (m/z): 376.2 [M−2HCl]$^+$.

Example 21

2-{4-[6-(4-ethoxyphenoxy)hexyl]piperazin-1-yl}thiazole hydrochloride

According to the same method as described in step 1.4 of Example 1, a white solid 0.32 g was obtained; the white solid was completely dissolved with acetone (10 mL), to which a saturated solution of HCl-diethyl ether was slowly added dropwise till pH=5, followed by filtering to obtain a white solid 0.38 g, yield 41.1%. mp: 222-224° C.; $^1$H-NMR (400 MHz, DMSO-d$_6$, δ ppm) δ 1.29-1.44 (m, 3H), 1.68-1.73 (m, 4H), 3.09-3.14 (m, 4H), 3.49-3.57 (m, 4H), 3.88-3.95 (m, 6H), 6.83 (s, 4H), 7.00 (d, 1H, J=4.0), 7.26 (d, 1H, J=3.6 Hz), 10.99 (s, 1H); ESI-MS (m/z): 390.1 [M−2HCl]$^+$.

Example 22

2-{4-[5-(4-tert-butylphenoxy)pentyl]piperazin-1-yl}thiazole hydrochloride

According to the same method as described in step 1.4 of Example 1, a white solid 0.30 g was obtained; the white solid was completely dissolved with acetone (10 mL), to which a saturated solution of HCl-diethyl ether was slowly added dropwise till pH=5, followed by filtering to obtain a white solid 0.12 g, yield 13.4%. mp: 240-242° C.; $^1$H-NMR (400 MHz, DMSO-d$_6$, δ ppm) δ 1.09 (t, 3H, J=7.6 Hz), 1.32-1.40 (m, 4H), 1.67-1.72 (m, 4H), 3.04-3.09 (m, 4H), 3.52-3.60 (m, 4H), 3.86-4.03 (m, 4H), 6.79 (d, 2H, J=8.4), 7.01 (d, 1H, J=3.6), 7.06 (d, 2H, J=8.4), 7.27 (d, 1H, J=3.6 Hz), 11.32 (s, 1H); ESI-MS (m/z): 374.3 [M−2HCl]$^+$.

Example 23

2-{4-[6-(4-isopropylphenoxy)hexyl]piperazin-1-yl}thiazole hydrochloride

According to the same method as described in step 1.4 of Example 1, a white solid 0.32 g was obtained; the white solid was completely dissolved with acetone (10 mL), to which a saturated solution of HCl-diethyl ether was slowly added dropwise till pH=5, followed by filtering to obtain a white solid 0.33 g, yield 35.8%. mp: 135-137° C.; $^1$H-NMR (400 MHz, DMSO-d$_6$, δ ppm) δ 1.16 (d, 6H, J=6.8 Hz), 1.35-1.47 (m, 4H), 1.68-1.74 (m, 4H), 2.82 (m, 3H), 3.08-3.13 (m, 4H), 3.45-3.57 (m, 4H), 3.91-4.00 (m, 4H), 6.83 (d, 2H, J=8.4), 6.98 (d, 1H, J=4.0), 7.13 (d, 2H, J=8.4 Hz), 7.23 (d, 1H, J=3.6 Hz), 10.93 (s, 1H); ESI-MS (m/z): 388.3 [M−2HCl]$^+$.

Example 24

Anti-picornaviral activity of the compounds of the present invention in in vitro model Test item: activity screening of compounds against enteroviruses EV71 and Cox A16 Test principle: using Vero cells as virus host, the cytopathic effect of Vero cells induced by the inhibition of compounds against enteroviruses EV71 and Cox A16 was measured.

Test Materials and Methods:

1. Virus strains: enteroviruses EV71 (Shenzhen 98) and Cox A16, passaging in the laboratory.

2. Sample treatment: Samples of compounds 1-23 in the examples were formulated into mother liquors with DMSO; when detected, the mother liquors were diluted with culture medium to certain concentrations, followed by a 4-fold dilution, totaling 8 dilutions.

3. Positive control: Con: ribavirin (RBV), Xinxiang Pharmaceutical Co., Ltd. (lot number 20080301). Ribavirin, which has different Chinese names, is a broad-spectrum potent antiviral drug, and is being widely used in the prevention and treatment of diseases induced by viruses including enteroviruses at present.

Test Method: Vero cells were incubated in a 96-well culture plate. After 24 hours, they were infected with EV71 and Cox A16 by adsorption for 2 hours. After discarding the virus solution, maintenance solutions containing different concentrations of samples and positive controls were added, and, at the same time, cell control wells and virus control wells were set. When the cytopathic effect (CPE) of the virus control group reached 4+, the cytopathic effects (CPE) of various groups were observed. The half inhibitory concentrations ($IC_{50}$) of the samples against EV71 and Cox A16 were respectively calculated according to the Reed-Muench method.

Activity screening data of positive controls Con1, Con2 and compounds 1-23 in the examples were listed in Table 7-1:

TABLE 7-1

Activity screening data of compounds

| Sample No. | Initial conc. (µg/ml) | $TC_{50}$ (µg/ml) | $TC_0$ (µg/ml) | CoxA16 $IC_{50}$ (µg/ml) | SI | EV71 $IC_{50}$ (µg/ml) | SI |
|---|---|---|---|---|---|---|---|
| Con | 2000 | 2000 | 500.0 | 363.11 | 5.5 | 517.4 | 3.9 |
| 1 | 200 | 100.0 | 50.0 | 25.0 | 4.0 | 36.31 | 2.8 |
| 2 | 200 | 25.0 | 12.5 | 1.97 | 12.7 | 7.87 | 3.2 |
| 3 | 200 | 79.37 | 12.5 | >12.5 | — | >12.5 | — |
| 4 | 200 | 12.5 | 3.13 | 1.97 | 6.3 | >3.13 | — |
| 5 | 200 | 6.25 | 3.13 | 1.57 | 4.0 | >3.13 | — |
| 6 | 200 | 6.25 | 3.13 | 1.57 | 4.0 | >3.13 | — |
| 7 | 200 | 19.84 | 3.13 | >3.13 | — | >3.13 | — |
| 8 | 200 | 25.0 | 12.5 | 4.96 | 5.0 | >12.5 | — |
| 9 | 200 | 6.25 | 3.13 | 3.13 | 2.0 | 1.97 | 3.2 |
| 10 | 200 | 25.0 | 12.5 | 12.5 | 2.0 | >12.5 | — |
| 11 | 200 | 6.25 | 3.13 | 3.13 | 2.0 | 1.57 | 4.0 |
| 12 | 200 | 25.0 | 12.5 | >12.5 | — | >12.5 | — |
| 13 | 200 | 25.0 | 12.5 | 7.87 | 3.2 | >12.5 | — |
| 14 | 200 | 31.5 | 12.5 | 6.25 | 5.0 | >12.5 | — |
| 15 | 200 | >200.0 | >200.0 | 100 | >2.0 | >200.0 | — |
| 16 | 200 | 25.0 | 12.5 | 4.30 | 5.8 | >12.5 | — |
| 17 | 200 | 4.96 | 0.78 | >0.78 | — | >0.78 | — |
| 18 | 200 | 4.96 | 0.78 | >0.78 | — | >0.78 | — |
| 19 | 200 | 79.37 | 12.5 | 12.5 | 6.3 | >12.5 | — |
| 20 | 200 | 63.0 | 3.13 | >3.13 | — | >3.13 | — |
| 21 | 200 | 25.0 | 3.13 | 3.13 | 8.0 | 1.97 | 12.7 |
| 22 | 200 | 25.0 | 12.5 | 6.25 | 4.0 | 1.97 | 12.7 |
| 23 | 200 | 19.84 | 3.13 | 0.57 | 34.8 | 1.97 | 10.1 |

The invention claimed is:

1. A compound or a pharmaceutically acceptable salt or hydrate thereof, which is selected from the group consisting of:
   2-{4-[5-(4-methoxyphenoxy)pentyl]-piperazin-1-yl}thiazole,
   2-{4-[5-(4-ethoxyphenoxy)pentyl]piperazin-1-yl}thiazole,
   2-{4-[5-(4-fluorophenoxy)pentyl]-piperazin-1-yl}thiazole,
   2-{4-[5-(4-ethylphenoxy)pentyl]piperazin-1-yl}thiazole,
   2-{4-[5-(4-isopropylphenoxy)pentyl]piperazin-1-yl}thiazole,
   2-{4-[5-(4-tert-butylphenoxy)pentyl]piperazin-1-yl}thiazole,
   2-{4-[5-(4-methylphenoxy)pentyl]piperazin-1-yl}thiazole,
   2-{4-[6-(4-methylphenoxy)hexyl]piperazin-1-yl}thiazole,
   2-{4-[6-(4-ethylphenoxy)hexyl]piperazin-1-yl}thiazole,
   2-[4-(6-phenoxyhexyl)piperazin-1-yl]thiazole,
   2-{4-[6-(4-tert-butylphenoxy)hexyl]piperazin-1-yl}thiazole,
   2-{4-[6-(4-fluorophenoxy)hexyl]piperazin-1-yl}thiazole,
   2-{4-[6-(4-chlorophenoxy)hexyl]piperazin-1-yl}thiazole,
   2-{4-[6-(4-bromophenoxy)hexyl]piperazin-1-yl}thiazole,
   2-{4-[5-(4-chlorophenoxy)pentyl]piperazin-1-yl}thiazole,
   2-{4-[5-(4-bromophenoxy)pentyl]piperazin-1-yl}thiazole,
   2-{4-[5-(4-bromophenoxy)pentyl]piperazin-1-yl}thiazole hydrochloride,
   2-[4-(5-phenoxypentyl)piperazin-1-yl]thiazole hydrochloride,
   2-{4-[6-(4-methoxyphenoxy)hexyl]piperazin-1-yl}thiazole hydrochloride,
   2-{4-[6-(4-ethoxyphenoxy)hexyl]piperazin-1-yl}thiazole hydrochloride,
   2-{4-[6-(4-ethylphenoxy)hexyl]piperazin-1-yl}thiazole hydrochloride, and
   2-{4-[6-(4-isopropylphenoxy)hexyl]piperazin-1-yl}thiazole hydrochloride.

2. A pharmaceutical composition comprising at least one compound or a pharmaceutically acceptable salt or hydrate thereof according to claim 1 and one or more pharmaceutically acceptable vehicles or excipients.

3. A method for the prevention and/or treatment of a disease associated with picornaviral infection, wherein the disease is selected from the group consisting of hand, foot and mouth disease, aseptic meningitis and brain stem encephalitis, comprising administering a prophylactically and/or therapeutically effective amount of at least one compound or a pharmaceutically acceptable salt or hydrate thereof according to claim 1 to a patient in need thereof.

* * * * *